(12) United States Patent
Khairoun et al.

(10) Patent No.: US 9,642,939 B2
(45) Date of Patent: May 9, 2017

(54) MACROPOROUS AND HIGHLY RESORBABLE APATITIC CALCIUM-PHOSPHATE CEMENT

(75) Inventors: Ibrahim Khairoun, Nantes (FR); Pierre Weiss, Saint Herblain (FR); Jean-Michel Bouler, Carquefou (FR)

(73) Assignees: GRAFTYS, Aix en Provence (FR); UNIVERSITE DE NANTES, Nantes (FR)

( * ) Notice: Subject to any disclaimer, the term of this patent is extended or adjusted under 35 U.S.C. 154(b) by 734 days.

(21) Appl. No.: 12/438,598

(22) PCT Filed: Aug. 23, 2007

(86) PCT No.: PCT/IB2007/002422
§ 371 (c)(1),
(2), (4) Date: Nov. 5, 2009

(87) PCT Pub. No.: WO2008/023254
PCT Pub. Date: Feb. 28, 2008

(65) Prior Publication Data
US 2010/0068243 A1 Mar. 18, 2010

Related U.S. Application Data

(60) Provisional application No. 60/839,697, filed on Aug. 24, 2006.

(30) Foreign Application Priority Data

Aug. 24, 2006 (EP) ..................................... 06291352

(51) Int. Cl.
| | | |
|---|---|---|
| A61K 33/00 | (2006.01) | |
| A61K 9/14 | (2006.01) | |
| A61K 33/42 | (2006.01) | |
| A61L 27/46 | (2006.01) | |
| A61L 24/00 | (2006.01) | |
| A61L 27/56 | (2006.01) | |
| A61L 27/58 | (2006.01) | |

(52) U.S. Cl.
CPC .......... *A61L 27/46* (2013.01); *A61L 24/0036* (2013.01); *A61L 24/0042* (2013.01); *A61L 24/0063* (2013.01); *A61L 24/0084* (2013.01); *A61L 27/56* (2013.01); *A61L 27/58* (2013.01); *A61L 2430/02* (2013.01)

(58) Field of Classification Search
None
See application file for complete search history.

(56) References Cited

U.S. PATENT DOCUMENTS

| | | | |
|---|---|---|---|
| 5,733,572 A * | 3/1998 | Unger et al. ................. | 424/450 |
| 5,976,234 A | 11/1999 | Chow et al. | |
| 6,206,957 B1 * | 3/2001 | Driessens et al. ............. | 106/35 |
| 6,558,709 B2 * | 5/2003 | Higham ....................... | 424/602 |
| 6,599,323 B2 | 7/2003 | Melican et al. | |
| 6,793,725 B2 * | 9/2004 | Chow et al. ................... | 106/35 |
| 2004/0024081 A1 | 2/2004 | Trieu et al. | |
| 2004/0137032 A1 * | 7/2004 | Wang ........................... | 424/423 |
| 2005/0084542 A1 | 4/2005 | Rosenberg et al. | |
| 2006/0233849 A1 | 10/2006 | Simon et al. | |

FOREIGN PATENT DOCUMENTS

| | | | |
|---|---|---|---|
| JP | H07-213598 | | 8/1995 |
| JP | 2001-259013 | | 9/2001 |
| WO | WO03024316 | * | 3/2003 |
| WO | WO 2006/030054 | | 3/2006 |

OTHER PUBLICATIONS

Greish et al., Composite formation from hydroxyapatite with sodium and potassium salts of phosphazene, J. of Mater. Sci. Med., vol. 16, pp. 613-620 (2005).*
Iooss et al. "A new injectable bone substitute combining poly(e-caprolactone) microparticles with biphasic calcium phosphate granules", Biomaterials, 22, 2001, pp. 27852794.*
Kurashina et al. "Bone response to hardened alpha-TCP", Japanese Journal of Oral and Maxillofacial Surgery, 38, 1992, pp. 325-330.*
Gauthier, et al. "Noninvasive Bone Replacement With a New Injectable Calcium Phosphate Biomaterial", Journal of Biomedical Materials Research, vol. 66, No. A, (Jul. 1, 2003), pp. 47-54.
Le-Ray, et al. "Vancomycin Encapsulation in Biodegradable Poly (E-Caprolactone) Microparticles for Bone Implantation. Implantation of the Formulation Process on Size, Drug Loading, in Vitro Release and Cytocompatibility", Biomaterials, Elsevier Science Publishers BV., Barking, GB, vol. 24, No. 3 (Feb. 2003) pp. 443-449.
Khairoun et al, "Improvement of Porosity of a Calcium Phosphate Cement by Incorporation of Biodegradable Polymer Microspheres", 2005, pp. 130-131, Trans Tech Publications, Switzerland.

* cited by examiner

*Primary Examiner* — Melissa Javier
(74) *Attorney, Agent, or Firm* — B. Aaron Schulman, Esq.; Stites & Harbison, PLLC.

(57) ABSTRACT

The present invention is directed to a novel cement powder comprising an organic component consisting of one or more biocompatible and bioresorbable polymers and an inorganic component consisting of one or more calcium phosphate compounds. The invention also relates to the apatitic CPC resulting from the mixing of said cement powder with a liquid phase and setting.

9 Claims, 3 Drawing Sheets

Figure 1:
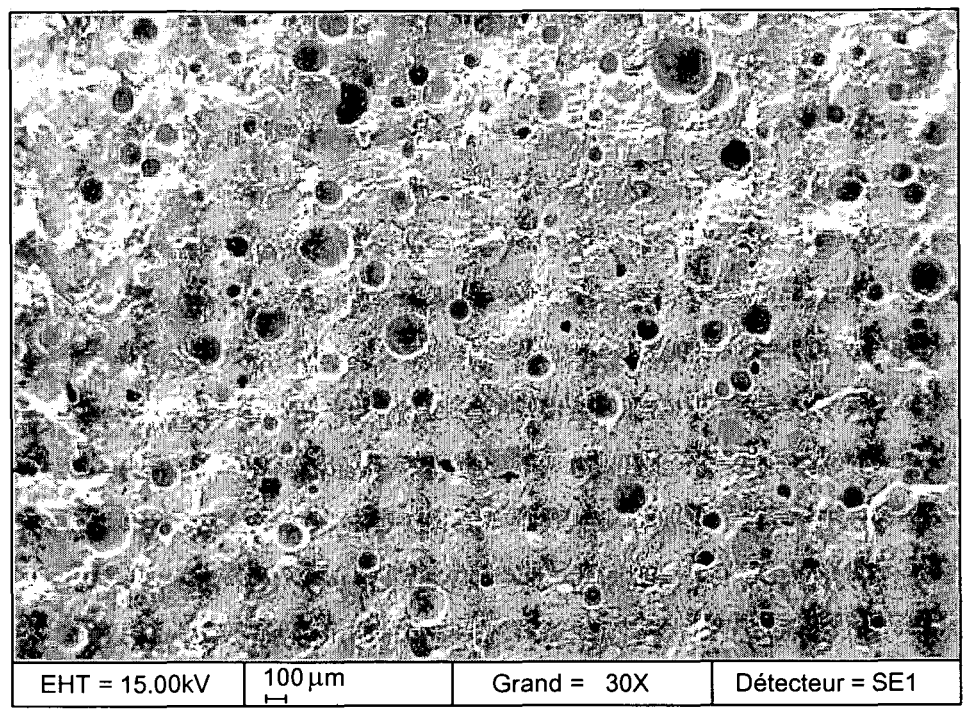

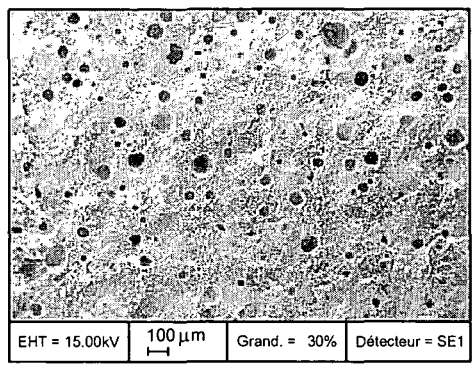 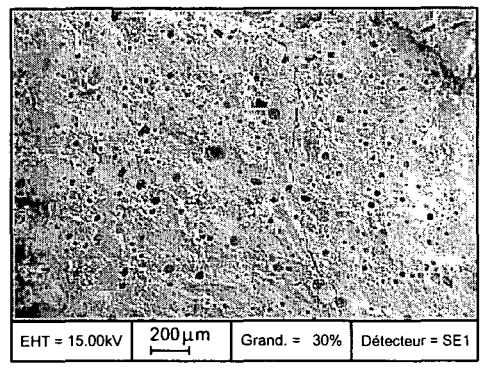
*FIG.3a*          *FIG.3b*
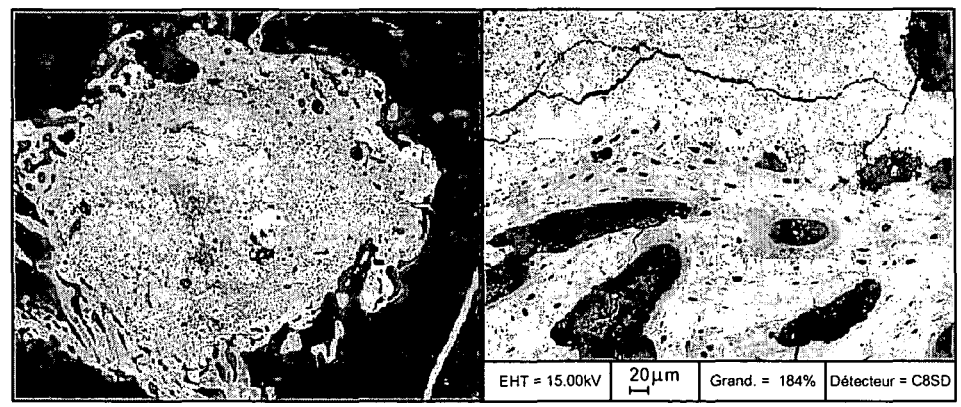
*FIG.4*

MACROPOROUS AND HIGHLY RESORBABLE APATITIC CALCIUM-PHOSPHATE CEMENT

CROSS REFERENCE TO RELATED APPLICATIONS

This application claims benefit of U.S. Provisional Application No. 60/839,697 filed Aug. 24,2006.

FIELD OF INVENTION

The invention relates to a macroporous and highly resorbable apatitic calcium-phosphate cement with a high compressive strength useful as bone cement.

BACKGROUND OF INVENTION

Bone is a composite of biopolymers, principally collagen, and an inorganic component identified as carbonate hydroxyapatite, approximated as $(Ca,Mg,Na,M)_{10}(PO_4, CO_3,HPO_4)_6(OH,Cl)_2$.

To date, a wide variety of implant materials have been used to repair, restore, and augment bone. The most commonly used implants include autologous bone, synthetic polymers and inert metals. Protocols using these materials have significant disadvantages that can include patient pain, risk of infection during operations, lack of biocompatibility, cost and the risk that the inserted hardware can further damage the bone. Therefore, a major goal of biomaterial scientists has been to develop novel bone substitutes that can be used as alternatives to these conventional techniques for skeletal repair.

Bone cements, such as cements based on polymethylmethacrylate (PMMA) offer certain advantages in avoiding the use of solid implants, but also have several disadvantages. Methacrylates and methacrylic acid are known irritants to living tissues, and when PMMA-based cements are cured in vivo, free radicals are generated, which can damage surrounding tissues. Moreover, the polymerization reaction for these materials is highly exothermic, and the heat evolved during curing can damage tissues.

The concept and potential advantages of an apatitic or calcium phosphate cement (CPC) as a possible restorative material was first introduced by LeGeros et al in 1982 ("Apatitic Calcium Phosphates: Possible Restorative Materials", J Dent Res 61(Spec Iss):343).

There are presently several CPC commercial products. CPC have the following advantages: malleability allowing them to adapt to the defect's site and shape. The introduction of injectable calcium phosphate cements greatly improved the handling and delivery of the cements and opened up areas of new applications for the CPC.

CPC systems consist of a powder and a liquid component. The powder component is usually made up of one or more calcium phosphate compounds with or without additional calcium salts. Other additives are included in small amounts to adjust setting times, increase injectability, reduce cohesion or swelling time, and/or introduce macroporosity.

The liquid component may consist of one or more of the following: saline, deionized water, dilute phosphoric acid, dilute organic acids (acetic, citric, succinic acid), sodium phosphate (alkaline or neutral), sodium carbonate or bicarbonate, sodium alginate, sodium bicarbonate, sodium citrate, and/or sodium chondroitin sulphate.

The currently available commercial CPCs suffer from some shortcomings such as absence of macroporosity, slow rate of bioresorbability and a frangible compressive strength. This leads to dangerous stress fractures.

Macroporosity is of great importance for bone regeneration as it facilitates bone cells colonisation of the material, angiogenesis, tissue ingrowth and reabsorption of the material.

Several methods of introducing macroporosity in CPCs have been disclosed.

One of them consists of liberation of $CO_2$ during the reaction of acid and $NaHCO_3$ in providing acid (citric acid) and $NaHCO_3$ or adding acidic sodium phosphate $(NaH_2PO_4)$ solution to $NaHCO_3$.

Other methods have been recommended as introduction of resorbable fibers, e.g. polygalactin; addition of soluble salts (e.g. calcium chloride and sodium or potassium hydroxide; addition of pore forming agents (e.g., sugar, $NaHCO_3$, calcium salts); using frozen sodium phosphate $(NaH_2PO_4)$ solution particles.

WO2006030054 suggests foaming of a calcium phosphate cement with the addition of surface active agents and the mechanical beating or stirring of same to form air bubbles providing microporosity.

SUMMARY OF INVENTION

Briefly, therefore, the present invention is directed to a novel cement powder comprising an organic component consisting of one or more biocompatible and bioresorbable polymers and an inorganic component consisting of one or more calcium phosphate compounds. Preferably, after mixing with a liquid phase and setting, this cement yields to an apatitic calcium phosphate cement with a macroporosity above 100 μm and a compressive strength above 10 MPa. The cement powder according to the invention is useful as a bone cement.

The inorganic component precipitates after dissolution in the liquid phase in a calcium-deficient apatite. This thus obtained apatite is degraded by chemical and cellular processes favoured by microporosity.

The polymers of the organic component swell in contact with the liquid phase. After setting, the polymers are integrated in the mineral part. They act as a binder between mineral particles and confer the biomechanical rheological and elastic properties to the CPC. Their further degradation results in tunnels and macropores interconnected. Interconnected macropores in the apatitic cement allow its passive resorption by dissolution through the biological fluids and its active resorption through the colonisation of the macropores by osteoclasts.

The invention also relates to the apatitic CPC resulting from the mixing of said cement powder with a liquid phase and setting. This CPC according the invention has macroporosity not exhibited by currently disclosed apatitic CPCs and a high compressive strength. These properties confer particular advantages as a high rate of resorbability and an elasticity very closed to natural bones.

The CPC according the invention can be used for dental and medical applications relating to bone repair, augmentation, reconstruction, regeneration, and osteoporosis treatment, and also for drug delivery, and as scaffolds for tissue engineering. Other potential dental applications are: repair of periodontal defects, sinus augmentation, maxillofacial reconstruction, pulp-capping materials, cleft-palate repair, and as adjuvants to dental implants. Additional medical applications include repair of large bony defects, repair of bone fractures caused by trauma, or associated with osteoporosis; for spine fusion, surgery revision, bone augmentation, and for bone reconstructions associated with cancer therapy.

DEFINITIONS

"Biocompatible" used herein means well tolerated by the host organism and which does not cause rejection reaction, toxic reaction, noxious lesion or noxious effect on its biological functions.

As used herein, a "bioresorbable polymer" is a polymer whose degradative products are metabolized in vivo or excreted from the body via natural pathways.

A "cement" is the result of the setting of a paste resulting from the mixing of a pulverulent solid phase and a liquid phase.

The "setting" of a cement means the hand-off autohardening at room or body temperature of the paste resulting from the mixing of the solid phase and the liquid phase.

An "injectable cement" means a cement paste sufficiently fluid to flow through a needle with a diameter of a few millimetres, preferably between 1 and 5 mm.

A "calcium phosphate cement" is a cement wherein the pulverulent solid phase is made of a calcium phosphate compound or a mixture of calcium and/or phosphate compounds.

An "apatitic" calcium phosphate cement crystallises in the hexagonal system having the formula $Ca_{5x}(PO_4)_{3x}(OH,Cl,F)_x$ with $x \geq 1$.

A calcium phosphate is said "amorphous" without crystalline structure.

A "macropore" is a pore with a diameter above 100 µm. The "macroporosity" is the state of cement which contains macropores with a diameter above 100 µm, preferably between 100 and 300 µm.

A "macroporosity above 200" means that the macropores of the cement have in average a diameter above 200 µm.

The "compressive strength" is the maximal compressive stress supported by the cement sample upon failure. It is expressed in MPa [Mnewtons/m²].

A "microparticle" has a diameter less than 1 mm.

A "microsphere" of polymer is a microparticle formed by a homogenous polymeric matrix with a diameter less than 1 mm, preferably between 100 and 300 µm, preferably 150 and 250 µm, more preferably between 80 and 200 µm.

A "microcapsule" of polymer is a hollow microsphere constituted by a polymeric envelope surrounding a reservoir with a diameter less than 1 mm, preferably between 100 and 300 µm, preferably 150 and 250 µm.

An "implant" is an object introduced in the body to replace in part or entirely a tooth, a joint, a bone or a cartilage.

A "minimally invasive surgery" means a technique of surgery that does not require a large incision but a few centimetres incision, preferably ≤5 cm.

Dendrimers are high size arborescent (dendritic) polymers produced by iterative processes from one molecule with at least three reactive sites.

Polysaccharides are a class of carbohydrates, such as starch and cellulose, consisting of a number of monosaccharides joined by glycosidic bonds. Polyphosphazenes have the general following formula with $n>1$.

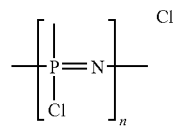

DETAILED DESCRIPTION OF INVENTION

The first object according to the invention consists in a cement powder comprising an organic component consisting of one or more biocompatible and bioresorbable polymers and an inorganic component consisting of one or more calcium phosphate compounds. This powder cement sets with a liquid phase in an apatitic calcium phosphate cement with a macroporosity above 100 µm, preferably between 100 and 300 µm, most preferably between 200 and 300 µm and a compressive strength above about 10 MPa, preferably above about 20 MPa, most preferably above about 25 MPa.

Preferably, this compressive strength is achieved with an amount of polymer in the cement powder between about 0.1 and about 30%, preferably about 0.5 and about 30%, more preferably about 1 to about 10%, the most preferably about 1 to about 5%.

This macroporosity is achieved with the degradation of the polymer microparticles integrated in the mineral part after setting. Preferably, the appropriate diameter of the polymer microparticles is between 20 and 300 µm, preferably 50 and 250 µm, more preferably 80 and 200 µm, the most preferably 100 and 200 µm.

Biocompatible and bioresorbable polymers useful in the invention include, for example, a polymer from the linear polyester family, such as polylactic acids, polyglycolic acids or poly(ε)caprolactone and their associated copolymers, e.g. poly(lactide-co-glycolide) at all lactide to glycolide ratios, and both L-lactide or D,L-lactide; collagen, polyphosphazenes, dendrimers and polysaccharides; polyorthoester, polyanhydride, polydioxanone, hyaluronic acid and polyhydroxybutyrate and their salts and mixtures thereof.

Polyphosphazenes, dendrimers, polysaccharides, poly(ε) caprolactone and their salts and mixtures thereof are preferred as the organic component of the cement powder according to the invention. In addition to their physical properties and good compressive strengths, these can be produced with appropriate resorption speed, hydrophilic properties and solubility. Then, this allows the control of their resorbability and the guided resorption-substitution of the CPC. Polyphosphazenes which can be used according to the invention are preferably selected from the group consisting of poly(ethyl oxybenzoate)phosphazene (PN-EOB), poly(propyl oxybenzoate) phosphazene (PN-POB), poly[bis (sodium carboxylatophenoxy)phosphazene] (Na-PCPP), poly[bis(potassium carboxylatophenoxy)phosphazene] (K-PCPP), poly[bis(ethyl alanato)phosphazene] (PAIaP), poly[bis(carboxylatophenoxy)phosphazene] (acid-PCPP), and their salts and mixtures thereof.

Polysaccharides and their salts and mixtures thereof are more preferred polymers used in the organic component of the cement powder according to the invention. Cellulose ethers and their salts and mixtures thereof are preferred polysaccharides used in the organic component of the cement powder according to the invention, more preferably selected from the group consisting of hydroxypropylmethylcellulose (HPMC), carboxymethylcellulose (CMC)

Biocompatible and bioresorbable polymers according to the invention can be used as fine powders, fibers or microparticles.

Polymer microparticles can be microspheres or microcapsules, preferably encapsulating one or several excipients such as saccharose, glucose, water, a gas as air, or one or several pharmaceutically active substances as an antibiotic, an anti-inflammatory drug, an anti-cancer drug, a drug against osteoporosis, a growth factor or a mixture thereof. Encapsulating methods are well known by the one skilled in the art.

Preferably, said polymer microparticles are poly($\epsilon$)caprolactone microspheres.

The organic component varies between about 0.1 and about 30%, preferably between about 0.5 and about 30%, more preferably between about 1 and about 10%, the most preferably between about 1 and about 5% by weight of the total amount of the cement powder according to the invention.

Preferably, the cellulose ethers amount varies between about 0.1 and about 5, preferably between about 1 and about 3%, more preferably between about 1 and about 2% by weight of the total amount of the cement powder according to the invention.

Calcium phosphate compounds useful in the invention include hydroxyapatite (HA) $Ca_{10}(PO_4)6(OH)_2$; amorphous calcium phosphate (ACP), $Ca_x(PO_4)y.H_2O$; monocalcium phosphate monohydrate (MCPH), $CaH_4(PO_4)_2.H_2O$; dicalcium phosphate dihydrate (DCPD), $CaHPO_4.2H_2O$, also called brusnite; dicalcium phosphate anhydrous (DCPA), $CaHPO_4$; precipitated or calcium-deficient apatite (CDA), $(Ca,Na)_{10}(PO_4,HPO_4)_6(OH)_2$; alpha- or beta -tricalcium phosphate ($\alpha$-TCP, $\beta$-TCP), $Ca_3(PO_4)_2$; and tetracalcium phosphate (TTCP), $Ca_4P_2O_9$.

Easily resorbable calcium phosphate compounds are preferred.

An inorganic component consisting of one or more calcium phosphate compounds selected from the group consisting of $\alpha$-TCP, $\beta$-TCP, ACP, MCPH, DCPA and mixtures thereof, is preferred.

An inorganic component consisting of one or more calcium phosphate compounds selected from the group consisting of $\alpha$-TCP, MCPH, DCPD and mixtures thereof, is more preferred.

An inorganic component comprising $\alpha$-TCP is more preferred. $\alpha$-TCP has the formula $\alpha$-$Ca_3(PO_4)_2$. $\alpha$-TCP is easily transformed in calcium-deficient hydroxyapatite (CDA) in aqueous solution. This property is used to form apatitic CPCs.

In a preferred embodiment, the cement powder according to the invention comprises at least about 40%, preferably about 50%, more preferably about 60%, still more preferably about 70%, the most preferably about 80% of $\alpha$-TCP.

In one embodiment, the inorganic component includes $\alpha$-TCP and ACP. ACP is the most soluble in the group of calcium phosphate compounds used in many CPCs. ACP can be made more or less stable (i.e. more or less soluble or more or less susceptible to transform to other calcium phosphates) depending on the ions incorporated in it. (LeGeros et al., (1973), "Amorphous calcium phosphates:synthetic and biological).

An inorganic component consisting of $\alpha$-TCP and DCPD or $\alpha$-TCP and MCPM, or $\alpha$-TCP and DCPD and MCPM is preferred.

The most preferred cement powder according to the invention comprises an inorganic component consisting in $\alpha$-TCP and DCPD, or $\alpha$-TCP and MCPM, or $\alpha$-TCP and DCPD and MCPM and an organic component consisting in HPMC or CMC or poly($\epsilon$)caprolactone or a mixture thereof.

The inorganic component can also comprise strontium (Sr), magnesium (Mg), gallium, or sulphates ions. For example, strontium nitrate $Sr(NO_3)_2$ are used. The addition of these ions allows to better control setting and to improve dissolution of the final product.

A second object according to the invention is an apatitic calcium phosphate cement as the final product resulting from the mixing between a cement powder according the invention, that is comprising an organic component consisting of one or more biocompatible and bioresorbable polymers and an inorganic component consisting of one or more calcium phosphate compounds, and a liquid phase and setting. A CPC according the invention has a macroporosity above 100 μm, preferably between 100 and 300 μm, most preferably between 200 and 300 μm and a compressive strength above about 10 MPa, preferably above about 20 MPa, most preferably above about 25 MPa.

The inorganic component of the CPC allows an intimate bond with the native bone and osteogenic properties. The organic component allows macroporosity interconnected in the mineral matrix and improves the cohesion, the elasticity, the rheological properties and the injectability of the cement.

An appropriate liquid phase includes one or more of the following: saline, deionized water, dilute phosphoric acid, dilute organic acids (acetic, citric, succinic acid), sodium phosphate, sodium carbonate or bicarbonate, sodium alginate, sodium bicarbonate, sodium chondroitin sulphate a $Na_2HPO_4$ aqueous solution and/or a $Na_2HPO_4/NaH_2PO_4$ aqueous solution.

Water, a $Na_2HPO_4/NaH_2PO_4$ aqueous solution, a $Na_2HPO_4$ aqueous solution, a NaCl solution or a sodium citrate solution, are preferred. For example, a solution of 2 to 3% by weight of $Na_2HPO_4$ in distilled water or a 0.9% NaCl solution can be used.

The pH of the liquid phase should be between 5 to 10, preferably between 5 and 9, most preferably between 5 and 7.

Preferably, the liquid phase/solid phase (L/S) ratio is between about 0.25 and about 0.7 ml/g, more preferably between about 0.3 and about 0.6 ml/g, the most preferably is about 0.4 ml/g or about 0.5 ml/g.

The setting time, which can range from about 10 to about 60 min, preferably about 10 to about 30 min, depends on the composition of the powder and liquid components, the powder-to-liquid ratio, proportion of the calcium phosphate components and the particle sizes of the powder components. The setting time of the cement is an important property of the cement. If the setting time is too fast, the surgeon does not have time to use the cement before it is hard. If the setting time is too long, the surgeon must wait until he/she can close the wound.

In a preferred embodiment, at least one of the components comprises a setting regulator, a setting accelerator or a setting retarder or both.

A very efficient way to accelerate the setting time is to have large concentrations of phosphate ions in the mixing solution. This can happen via two ways: (i) a soluble phosphate salt is added as a powder in the cement formulation. Upon contact with the mixing solution, the phosphate salt dissolves, and hence accelerates the chemical reaction using up phosphate (LeChatelier principle); (ii) a soluble phosphate salt is pre-dissolved in the mixing liquid phase. Examples of soluble phosphate salts are $Na_2HPO_4$, $NaH_2PO_4$, $K_2HPO_4$, $KH_2PO_4$, $NH_4H_2PO_4$. Typical concentrations in the mixing liquid phase are in the range of 0.05 to 1.00 M. Another way to accelerate the setting reaction is to add germs for apatite crystal growth, as the nucleation step of the setting reaction is a limiting factor. Typically, apatite crystals can be used, preferably a calcium-deficient hydroxyapatite or hydroxyapatite powder. Small amounts (a few weight percents) are sufficient to drastically reduce the setting time.

When the setting time is too short, various setting additives can be added to increase the setting time. Typical examples are compounds which inhibit the nucleation and/or growth of apatite crystals. Common examples are pyrophosphate, citrate or magnesium ions. One particularly interesting compound is calcium carbonate. The one skilled in the art would obtain the appropriate setting time with routine assays.

Preferably, a CPC according to the invention is injectable. Indeed, in recent years, the occurrence of osteoporotic fractures has dramatically increased. Considering the lack of adequate cure and the increasing number of elderly people, this trend is expected to continue. Osteoporotic fractures are often very difficult to repair, because the bone is very weak. It is therefore not possible to insert screws to hold osteosynthesis plates. A way to solve the problem is to inject a CPC into the osteoporotic bone to reinforce it. The injection of a CPC into an osteoporotic bone is only possible if the cement is well injectable.

In order to prevent any extravasation of the cement into the tissues surrounding bone, it is very important to visualise the cement. The easiest way is to increase the radio-opacity of the cement, for example by means of contrasting agents. For example, metallic powders of tantalum, titanium or tungsten can be used. It might be preferable to use liquid agents in partially bioresorbable cements, such as iodine compounds as iopamidol, iohexyl and iotrolan. Preferably, barium sulphate is used.

Quite often, bone defects are not due to a traumatic event, but to a disease, e.g. bone tumour, infection, etc. . . . In these cases, it is interesting to incorporate drugs in the cement, in particular pharmaceutically or physiologically active substances, preferably antibiotics, anti-inflammatory drugs, anti-cancer drugs, drugs against osteoporosis, peptides, and proteins such as growth factors. Owing to their structure and their dissolution property, the calcium phosphate cements are able to slowly release the active ingredients into the environment within a few days after implantation. These active ingredients can also be encapsulated in a microcapsule of a biocompatible and bioresorbable polymer of the organic component of the CPC according to the invention.

Another object of the invention is the in vivo, in vitro or ex vivo use of a CPC according to the invention as a scaffold for tissue engineering.

The CPC according to the invention can also be employed in vivo, in vitro or ex vivo to produce a dental or a bony implant.

A further object of the invention is a dental or a bony implant consisting of a moulding of a CPC according to the invention.

A further object of the invention is the use of an injectable CPC according to the invention to fill a bony defect or fracture caused by trauma or associated with osteoporosis. This includes a surgery step but injectable CPCs according to the invention can get to inaccessible parts of the body and are suited for minimally invasive surgery procedures that are intended to reduce damage and pain while hastening return to function. This method of treatment comprises the introduction in the bony defect or fracture through a needle of an injectable CPC according to the invention.

A further object of the invention is the use of an injectable CPC according to the invention for the preparation of a medicament for the treatment of a bony defect or fracture caused by trauma or associated with osteoporosis.

For example, they can be employed in percutaneous vertebroplasty. This consists of a percutaneous puncture method to stabilize and straighten vertebral collapse of the thoracic and lumbar spinal column, most often as a result of osteoporosis.

In the course of osteoporosis, a very painful vertebral collapse can occur in the region of the thoracic (TSC) and lumbar (LSC) spinal column as a result of the reduced load-bearing capacity of the skeletal frame. This results in more or less distinct deformation of the vertebrae, and even in vertebral collapse. Both cases are easily recognizable by x-ray. Even a complete vertebral collapse and distinct deformation of the entire spinal column is possible.

Under local anesthetic, or, if desired, under full narcosis, a thin puncture needle is inserted to the vertebra, e.g. under x-ray guidance. At a certain point of the vertebra (the so-called pedicel), the bone can be punctured by the needle without risk. Afterwards, fluid bone cement is injected into the vertebra via the puncture needle; after the cement hardens, the vertebra is stabilized (vertebroplasty). If the vertebra is severely deformed (e.g. in the case of a wedge-like formation), the collapsed vertebra is straightened before the cement is injected. A balloon is hereby inserted into the vertebra via the puncture needle and inflated with fluid under high pressure. Following a successful straightening, the balloon is removed and the resulting cavity is filled with bone cement (balloon-kyphoplasty).

FIG. 1: Scanning electron microscopy (SEM) after 24 hours setting of a CPC prepared with a cement powder consisting of α-TCP (79%), DCPD (10%), MCPH (10%) and HMPC showing macropores of about 150 μm of main diameter.

Figure 2:
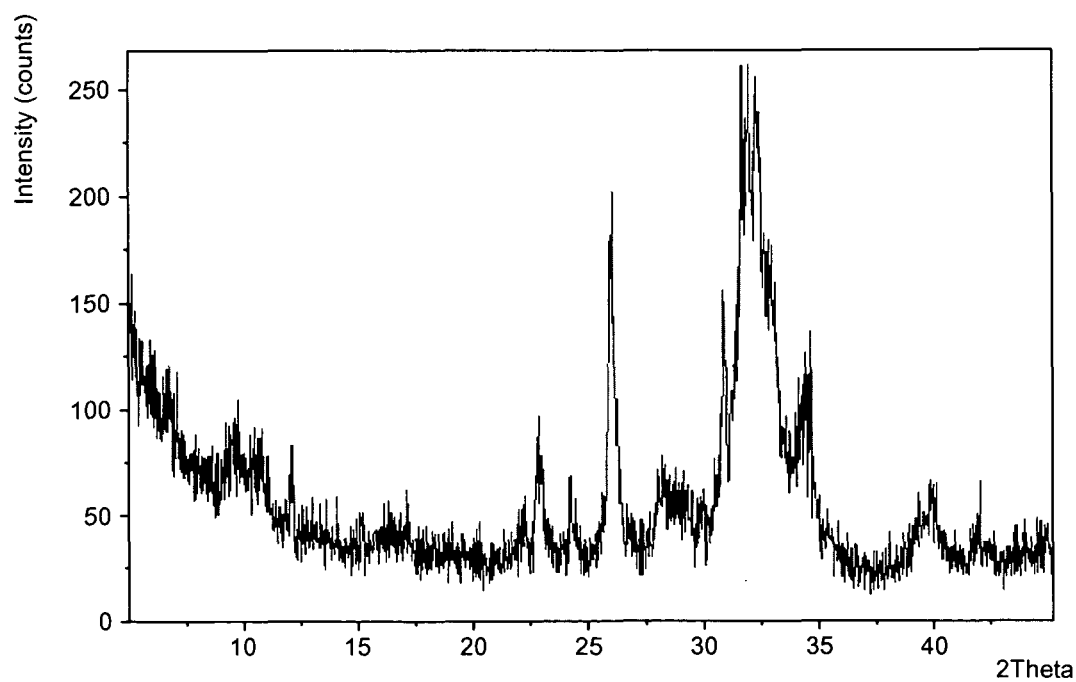

FIG. 2: X-ray diffraction spectrum of the final product of the reaction of a CPC prepared with a cement powder consisting of α-TCP (79%), DCPD (10%), MCPH (10%) and HMPC.

FIG. 3: Scanning electron microscopy (SEM) after 24 hours setting of a CPC prepared with a cement powder consisting of α-TCP (88%), HPMC (%), and DCPD (10%) (FIG. 3*a*) or MCPH (10%) (FIG. 3*b*).

FIG. 4: Scanning electron microscopy (SEM) of a rabbit femur defect 3 weeks after the implantation of a CPC prepared with a cement powder consisting of α-TCP (62%), $CaHPO_4$ (26%), $CaCO_3$ (8%) and HPMC (K15M) (4%).

Figure 5:
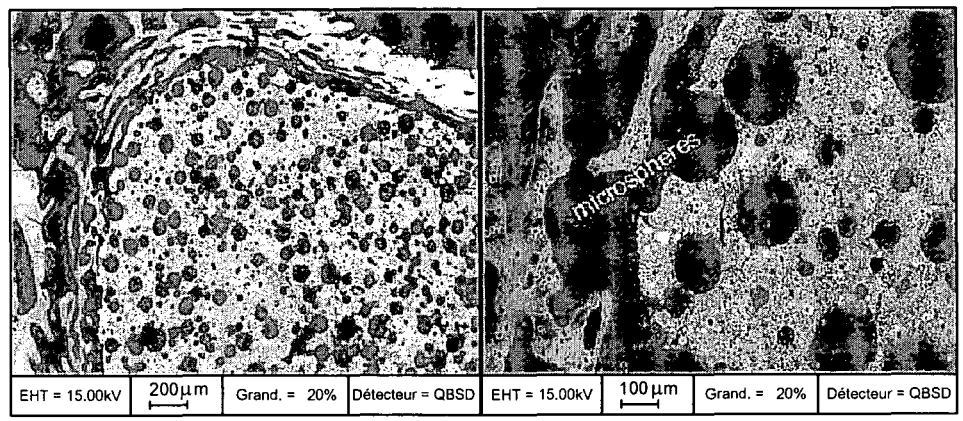

FIG. 5: Scanning electron microscopy (SEM) of a rabbit femur defect 3 weeks after the implantation of a CPC prepared with a cement powder consisting of α-TCP (51%), $CaHPO_4$ (20%), $CaCO_3$ (4%) and Poly(ε)caprolactone microspheres (25%).

Figure 6:
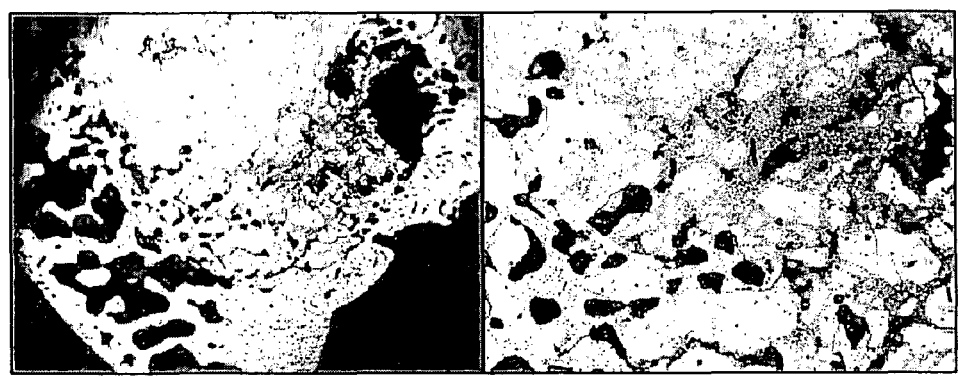

FIG. 6: Scanning electron microscopy (SEM) of a rabbit femur defect 6 weeks after the implantation of a CPC prepared with a cement powder consisting of α-TCP (88%), DCPD (5%), MCPM (5%), and E4M (2%).

The following examples illustrate and describe preferred embodiments of the invention.

EXAMPLES

Example 1

Preparation of poly(ε-caprolactone) Microspheres 1 g of poly(ε-caprolactone) (Tone® P787, Union Carbide SA, France) has been dissolved in 15 mL of Recaptur dichloromethane (Prolabo, France). This solution has been emulsified in an aqueous solution (1 L) of methylcellulose (Méthocel® A15LV premium EP, Colorcon, France) (0.75 g) at 4° C., under constant shaking (550 rpm), for 90 min. The resulting emulsion is then added to 1 litre of distilled water. The resulting suspension is then filtered in vacuum. The microspheres are then washed with 1 litre of distilled water and dried at room temperature for 24 h.

Example 2

Preparation of poly(ε-caprolactone) Microcapsules Encapsulating Water

The same process as Example 1 is used to produce microcapsules of poly(ε-caprolactone) encapsulating water except for adding of water in the polymer before the emulsion.

Example 3

Preparation and Characterization of Apatitic Calcium Phosphate Cements According to the Invention the inorganic component consists of α-TCP.

The organic component consists of microspheres or microcapsules of poly(ε-caprolactone) encapsulating water.

An aqueous solution of $Na_2HPO_4$ (3%) is used as liquid phase.

Different cements with different liquid/powder ratios (L/P) have been prepared (0.32 mL.g$^{-1}$<L/P<0.40 mL.g$^{-1}$) and different percentages of microparticles of poly(ε-caprolactone) from 0 to 10%.

The inorganic and organic components are mixed with the liquid phase and the mixing is placed in a cylinder-shaped mould. After 15 min, the mould is placed is a 0.9% NaCl solution at 37° C. These conditions simulate the in vivo conditions. The saline solution is changed every three days. The incubation time is one week or one month.

After the incubation period, the cylinders are taken out of moulds and assayed.

Table 1 summarizes the different conditions.

TABLE 1

| No. | L/P (mL · g$^{-1}$) | α-TCP weight (g) | Liquid phase Volume (mL) | Microparticles (%) | Microparticles weight (g) | Incubation time |
|---|---|---|---|---|---|---|
| 1 | 0.32 | 6.25 | 2 | 0 | 0 | 1 week |
| 2 | 0.40 | 5.00 | 2 | 0 | 0 | 1 week |
| 3 | 0.32 | 6.25 | 2 | 0 | 0 | 1 week |
| 4 | 0.40 | 5.00 | 2 | 0 | 0 | 1 week |
| 5 | 0.32 | 2.94 | 2 | 5 | 0.31 | 1 week |
| 6 | 0.40 | 7.13 | 3 | 5 | 0.38 | 1 week |
| 7 | 0.32 | 5.94 | 2 | 5 | 0.31 | 1 month |
| 8 | 0.40 | 6.75 | 3 | 10 | 0.75 | 1 month |
| 9 | 0.32 | 5.63 | 2 | 10 | 0.63 | 1 month |
| 10 | 0.32 | 2.87 | 1 | 10 (encapsulating water) | 0.32 | 1 week |

The samples are assayed by mercury porosimetry and the results are summarized in Table 2.

TABLE 2

| No. | Porosity (%) | Density (g/mL) | Diameter in average (μm) |
|---|---|---|---|
| 1 | 27 | 1.85 | 0.018 |
| 2 | 36 | 2.5 | 0.011 |

TABLE 2-continued

| No. | Porosity (%) | Density (g/mL) | Diameter in average (μm) |
|---|---|---|---|
| 5 | 27 | 2.20 | 0.011 |
| 6 | 37 | 1.98 | 0.012 |
| 7 | 27 | 2.34 | 0.011 |
| 8 | 37 | 2.10 | 0.012 |
| 9 | 28 | 2.19 | 0.011 |
| 10 | 45 | 2.74 | 0.0154 |

Example 4

α-tricalcium Phosphate Preparation

The preparation of α-tricalcium phosphate (α-TCP) was carried out by reacting in solid state, a stoichiometric mixture (molar ratio=2:1) of $CaHPO_4$ and $CaCO_3$, and subsequent cooling (quenching) in air down to room temperature.

The reaction product obtained was α-TCP containing impurities of β-TCP due to the quenching.

After crushing and milling of the α-TCP, a sieved fraction was selected with diameters ranging from 0.1 to 80 μwherein about 60% of the particles had an average particle size of 15 μm.

This α-TCP powder was used as the main part of the inorganic solid phase of the CPCs prepared in all the following experiments.

Example 5

Materiel and Methods of the Preparation of the α-TCP Based CPCs Assayed in the Following Examples The following polymers have been introduced in the α-TCP based powder calcium phosphate cements: hydroxypropylmethylcellulose (HPMC), carboxymethylcellulose (CMC), sodium alginate and poly(ε)caprolactone. HPMC and CMC (Colorcon, Inc.) were used as purchased.

Three types of HPMC (E4M, F4M and K15M) have been used. They have identical chemical structure but differ by their hydroxypropyl, hydroxyethyl or methoxyl content and substitution degrees (Table 3). K15M has a high molecular weight compared to E4M and F4M, which both have slightly different molecular weights.

TABLE 3

Different HPMC used as powders

| HPMC | DS Methoxyl | Methoxyl % | MS Hydroxypropyl | Hydroxypropyl % |
|---|---|---|---|---|
| METHOCEL E (E4M) | 1.9 | 29 | 0.23 | 8.5 |
| METHOCEL F (F4M) | 1.8 | 28 | 0.13 | 5.0 |
| METHOCEL K (K15M) | 1.4 | 22 | 0.21 | 8.1 |

Poly(ε)caprolactone was prepared by the method of LeRay A M et al (Biomaterials. 2001 Oct.; 22(20):2785-94) and a sieve fraction of 80-200 μm were used as microspheres.

Sodium alginate was used as purchased.

The liquid-to-powder ratios (L/P) used for the experiments were 0.40 and 0.50 ml/g. The liquids used as liquid phases of the cements were 3% solution of $Na_2HPO_4$ in distilled water, 3% solution of $Na_2HPO_4/NaH_2PO_4$ (pH 7.4) in distilled water and saline solution (0.9% NaCl).

The different CPCs were moulded in cylinders, 12 mm high and 6 mm in diameter, which were stored for 24 h and 36 h in saline solution at 37° C. The hardened cylinders were removed from the moulds prior to determination of the compressive strength and porosity measurements.

The initial and final setting times were determined at room temperature (20° C.±1) according to ASTM C266-8 standard by means of Gilmore needles. The compressive strength was determined using a Texture Analyser. The final reaction product was determined by means of X-ray diffractometry.

The study of the morphology evolution of the crystalline structures formed during the cement setting process was carried out by examining the fractured surfaces of samples by scanning electron microscopy.

Example 6

Comparison of Different Liquid Phases and Different Concentrations of HPMC

The inorganic component of the cement powders was composed of α-TCP (79%), dicalcium phosphate dihydrate (DCPD; $CaHPO_4.2H_2O$) (10%) and monocalcium phosphate monohydrate (MCPH; $Ca(H_2PO_4).H_2O$) (10%).

Different combinations with HMPC (E4M) and liquid phases were assayed. To prepare the cement samples, the cement powder was mixed with the liquid phase for 30 seconds at a L/P ratio of 0.40 ml/g. The following Table 4 summarizes the results of setting times, compressive strengths and morphologies of the set samples.

The nature of the liquid phase and the polymer concentration influence the setting time of the cement, meanwhile the compressive strength is only slightly affected by these parameters.

Scanning electron microscopy (SEM) showed an open morphology (FIG. 1) and presence of macroporosity after 24 hours setting with macropores of about 150 μm of main diameter.

The final product of the reaction was a calcium deficient apatite as determined by X-ray diffraction (FIG. 2)

Example 7

Comparison of Different Types of HPMC

Cement powder samples were prepared with α-TCP (84%), DCPD (5%) and MCPH (10%) combined with different HPMC samples (E4M, F4M and K15M) at 1% in weight.

The cement pastes were prepared with a 3% solution of $Na_2HPO_4/NaH_2PO_4$ (pH 7.4) and a L/P ratio of 0.40 ml/g.

After mixing the liquid phase and the cement powder during 30 seconds in a mortar, the resulting pastes had initial setting times respectively of 17 min, 25 min and 27 min for the cements prepared with K15M, F4M and E4M.

The results showed that the methoxyl content of HPMC is a parameter which influences the setting time of the reaction. On the contrary, the molecular weight and the hydroxypropyl content have a lower impact on the setting time.

The final product of the setting reaction for all samples was a calcium deficient apatite.

Example 8

Comparison of a combination α-TCP/DCPD/HPMC with a Combination α-TCP/MCPH/HPMC

Cement powder samples were prepared with α-TCP (88%) and DCPD (10%) or MCPH (10%) combined HPMC (E4M) at 2% in weight.

TABLE 4

| α-TCP (%) | DCPD (%) | MCPH (%) | HPMC (%) | Liquid phase | Initial setting time (min) | Compressive strength (MPa) |
|---|---|---|---|---|---|---|
| 79 | 10 | 10 | E4M 1% | $Na_2HPO_4/NaH_2PO_4$ | 34 | 12 |
|  |  |  |  | NaCl (0.9%) | 25 | 11 |
|  |  |  |  | $Na_2HPO_4$ | 16 | 11 |
| 78 | 10 | 10 | E4M 2% | $Na_2HPO_4/NaH_2PO_4$ | 45 | 10 |
|  |  |  |  | NaCl (0.9%) | 28 | 12 |
|  |  |  |  | $Na_2HPO_4$ | 25 | 10 |

The cement pastes were prepared with different liquid phases: 3% solution of $Na_2HPO_4/NaH_2PO_4$ (pH 7.4) in distilled water or 3% solution of $Na_2HPO_4$ in distilled water or 0.9% solution of NaCl. The L/P ratio was 0.40 ml/g.

After mixing the liquid phase and the cement powder during 30 seconds in a mortar, the resulting pastes showed the following results (Table 5).

The samples prepared with α-TCP and DCPD showed a longer setting time compared to that prepared with α-TCP and MCPH.

After setting, the final product of reaction was a calcium deficient apatite, and evident macroporosity was observed after 24 hours setting for all the cement samples.

The pores created by the combination α-TCP (88%), DCPD (10%) (FIG. 3a) were greater that those created by the combination α-TCP (88%), MCPH (10%) (FIG. 3b).

TABLE 5

| α-TCP (%) | DCPD (%) | MCPH (%) | HPMC (%) | Liquid | Initial setting time (min) | Compressive strength (MPa) |
|---|---|---|---|---|---|---|
| 88 | 10 | 0 | E4M 2% | $Na_2HPO_4/NaH_2PO_4$ | >60 | — |
|  |  |  |  | NaCl (0.9%) | >60 | — |
|  |  |  |  | $Na_2HPO_4$ | >60 | 14 |
| 88 | 0 | 10 | E4M 2% | $Na_2HPO_4/NaH_2PO_4$ | 33 | — |
|  |  |  |  | NaCl (0.9%) | 28 | — |
|  |  |  |  | $Na_2HPO_4$ | 20 | 8 |

Example 9

Preparation of CPCs with CMC and Sodium Alginate

Cement powder samples were prepared with α-TCP (86%), and DCPD (10%) combined sodium alginate or CMC at 4% in weight.

The cements were prepared with the liquid phase NaCl (0.9%) and a L/P ratio of 0.40 ml/g.

After mixing the liquid phase and the cement powder during 30 seconds in a mortar, the resulting pastes showed the following results (Table 6).

The samples prepared with sodium alginate showed a drastically retarded setting time (>120 minutes). After 24 h of setting, the presence of DCPD was still evident, the hydration of α-TCP and its precipitation into apatite was not complete.

The cement samples prepared with CMC showed an evident open structure with macroporosity. The CMC allowed the transformation of α-TCP to calcium deficient apatite.

TABLE 6

| α-TCP (%) | DCPD (%) | Polymer (%) | Liquid | Compressive strength (MPa) |
|---|---|---|---|---|
| 86 | 10 | Sodium alginate (4%) | NaCl (0.9%) | 4 (24 h) |
|  |  |  |  | 6 (36 h) |
| 86 | 10 | CMC (Blanose 7HXF) (4%) | NaCl (0.9%) | 10 (24 h) |
|  |  |  |  | 13 (36 h) |

Example 10

In Vivo Implantation of α-TCP Based CPCs with HPMC or Poly(ε)caprolactone Microspheres for 3 Weeks Two cement powder formulations were assayed for animal studies:
(a) α-TCP (62%), $CaHPO_4$ (26%), $CaCO_3$ (8%) and HPMC (K15M) (4%), and
(b) α-TCP (51%), $CaHPO_4$ (20%), $CaCO_3$ (4%) and Poly (ε)caprolactone microspheres (25%).

Cement pastes were prepared by mixing the sterilized cement powder and a sterilized solution of NaCl (0.9%). The L/P ratio was 0.40 ml/g.

Both cements showed a compressive strength of 25 MPa after 48 h setting.

The cement pastes were injected into a surgically created bone defect (6 mm diameter) in a rabbit femur. Implantations were performed under general anaesthesia. The rabbits were sacrificed after 3 weeks of implantation.

The results showed that the new bone formed with composition (a) had a good quality and was comparable to the host bone. The new bone was observed directly in contact with the implant without an intervening layer. After 3 weeks, an open structure and porosity was observed in the set cement (FIG. 4)

The composition (b) showed a good distribution of the poly(ε)caprolactone microspheres in the cement matrix. After degradation, they allowed to create an open structure with macropores ranging from 80 to 200 μm (FIG. 5).

Example 11

In Vivo Implantation of α-TCP Based CPCs with HPMC for 6 Weeks

A formulation α-TCP (88%), DCPD (5%), MCPM (5%), and E4M (2%) was assayed for animal studies for 6 weeks. The cement pastes were prepared by mixing sterilized cement powder and liquid phase.

The L/P ratio was 0.50 ml/g. The liquid phase was a 3% solution of $Na_2HPO_4/NaH_2PO_4$ (pH 7.4) in distilled water.

The cement pastes were injected into a surgically created bone defect (6 mm diameter) in a rabbit femur. Implantations were performed under general anaesthesia. The rabbits were sacrificed after 6 weeks of implantation.

The new bone was observed directly in contact with the implant without an intervening layer. After 6 weeks, new bone was formed surrounding the implant, and the bone growth has started with a great dissolution of the implant from the periphery (contact with host bone) to the core of the implant (FIG. 6).

The invention claimed is:

1. An injectable calcium phosphate cement comprising one or more calcium phosphate compounds, microparticles of hydroxypropylmethylcellulose (HPMC) with a diameter between 20 and 300 μm, and an aqueous solution of $Na_2HPO_4$;
   wherein the one or more calcium phosphate compounds comprises at least 70 % of an α-tricalcium phosphate (α-TCP);
   and wherein the calcium phosphate cement is made by forming a power mixture comprising the one or more calcium phosphate compounds, the HPMC in an amount of about 1% to about 3% by weight of the total amount of the cement powder, and the α-TCP and then mixing the resulting powder mixture with the aqueous solution of Na2HPO4 to form the injectable calcium phosphate cement.

2. The injectable calcium phosphate cement according to claim 1, wherein said calcium phosphate compounds are selected from the group consisting of hydroxyapatite (HA), amorphous calcium phosphate (ACP), monocalcium phosphate monohydrate (MCPH), dicalcium phosphate dihydrate (DCPD), dicalcium phosphate anhydrous (DCPA), precipitated or calcium-deficient apatite (CDA), α-tricalcium phosphate (α-TCP), β-tricalcium phosphate (β-TCP), tetracalcium phosphate (TTCP), and mixtures thereof.

3. The injectable calcium phosphate cement according to claim 2, wherein said calcium phosphate compounds are selected from the group consisting of α-TCP, MCPH, DCPD, and mixtures thereof.

4. The injectable calcium phosphate cement according to claim 1, wherein said calcium phosphate compounds consists of α-TCP and DCPD.

5. The injectable calcium phosphate cement according to claim 1, wherein said power mixture consists of a mixture of α-TCP, DCPD, and HPMC.

6. The injectable calcium phosphate cement according to claim 1, wherein the aqueous solution of Na2HPO4 and powder mixture is in a ratio of about 0.3 to about 0.6 mL/g.

7. The injectable calcium phosphate cement according to claim 1, further comprising one or more ingredients selected from the group of antibiotics, anti-inflammatory drugs, anti-cancer drugs, drugs against osteoporosis, and growth factors.

8. A scaffold for tissue engineering comprising the injectable calcium phosphate cement according to claim 1.

9. A dental or bony implant consisting of a molding of the injectable calcium phosphate cement according to claim 1.

* * * * *